United States Patent
Doi et al.

(10) Patent No.: US 9,563,045 B2
(45) Date of Patent: Feb. 7, 2017

(54) SURGICAL MICROSCOPE APPARATUS AND SEALED DRAPE

(71) Applicant: MITAKA KOHKI CO., LTD., Tokyo (JP)

(72) Inventors: Masao Doi, Tokyo (JP); Yusuke Nakata, Tokyo (JP)

(73) Assignee: MITAKA KOHKI CO., LTD., Tokyo (JP)

( * ) Notice: Subject to any disclaimer, the term of this patent is extended or adjusted under 35 U.S.C. 154(b) by 0 days.

(21) Appl. No.: 13/967,588

(22) Filed: Aug. 15, 2013

(65) Prior Publication Data
US 2014/0055850 A1 Feb. 27, 2014

(30) Foreign Application Priority Data
Aug. 22, 2012 (JP) ................................. 2012-183003

(51) Int. Cl.
*G02B 21/00* (2006.01)

(52) U.S. Cl.
CPC ........... *G02B 21/0012* (2013.01); *A61B 46/10* (2016.02); *A61B 90/20* (2016.02); *F04C 2270/0421* (2013.01)

(58) Field of Classification Search
CPC .................. G02B 21/0012; G02B 27/0006
USPC .................. 359/507–514, 368–398
See application file for complete search history.

(56) References Cited

U.S. PATENT DOCUMENTS

| 5,122,904 | A | 6/1992 | Fujiwara et al. |
| 5,970,980 | A | 10/1999 | Adair |
| 7,846,086 | B2 | 12/2010 | Brenner et al. |
| 2003/0066534 | A1 | 4/2003 | Spetzler et al. |
| 2004/0138650 | A1 | 7/2004 | Nakamura |
| 2005/0161176 | A1 | 7/2005 | Brenner et al. |

FOREIGN PATENT DOCUMENTS

| JP | 06-269461 | 9/1994 |
| JP | 2988980 | 10/1999 |
| JP | 2003-220077 | 8/2003 |
| JP | 2010-46117 | 3/2010 |

OTHER PUBLICATIONS

Japan Office action, mail date is Feb. 18, 2014.
EPO Search report, Dec. 2, 2013.
Japan Office action, mail date is May 20, 2014.

*Primary Examiner* — Bumsuk Won
*Assistant Examiner* — Tamara Y Washington
(74) *Attorney, Agent, or Firm* — Greenblum & Bernstein, P.L.C.

(57) ABSTRACT

At a front end of the lateral arm of a surgical microscope apparatus, the apparatus has an intake port. A band is tied around the front end of the lateral arm so that a drape is drawn only to a surgical microscope. Drawing the drape to the surgical microscope results in clearing the field of vision of a surgeon. Part of the drape around the lateral arm and a longitudinal arm is not drawn, to cause no hindrance in operability of the surgical microscope. The lateral arm and the like are hollow to form an inner ventilating path without separately preparing ventilating tubes or the like for ventilation.

2 Claims, 5 Drawing Sheets

US 9,563,045 B2

SURGICAL MICROSCOPE APPARATUS AND SEALED DRAPE

BACKGROUND OF THE INVENTION

1. Field of the Invention

The present invention relates to a surgical microscope apparatus used with a drape that covers the apparatus.

2. Description of Related Art

The surgical microscope apparatus suspends a surgical microscope in midair and is used for, for example, neurosurgery. The apparatus includes a stand that is set on a floor, a longitudinal arm that is uprightly and pivotally supported with the stand, and a lateral arm that has a base end pivotally supported at an upper end of the longitudinal arm and horizontally extends from the upper end of the longitudinal arm, the surgical microscope being suspended from a front end of the lateral arm.

The surgical microscope and part of the horizontal and longitudinal arms are covered with a drape to secure an aseptic condition.

If the drape loosens and sags, it will obstruct the visibility of a surgeon. To deal with this problem, Japanese Patent Publication No. 2988980 (Patent Literature 1) discloses a technique of drawing air from the inside of the drape so that the drape may tightly be attached to the surgical microscope apparatus.

SUMMARY OF THE INVENTION

This related art, however, pulls the drape not only from around the surgical microscope but also from around the lateral atm to tightly attach the drape to the lateral arm. The tightly attached drape prevents a free movement of the lateral arm, thereby deteriorating the operability of the surgical microscope apparatus.

The present invention provides a surgical microscope apparatus capable of drawing air only from around a surgical microscope covered with a drape.

According to an aspect of the present invention, the surgical microscope apparatus has a stand body, a longitudinal arm pivotally supported with the stand body, a lateral arm whose base end is pivotally supported at an upper end of the longitudinal arm, a surgical microscope supported in the vicinity of a front end of the lateral arm, and a drape distributing over a predetermined area of the apparatus ranging from the surgical microscope to the longitudinal arm. According to this aspect of the present invention, the apparatus includes a hollow structure provided for each of the vertical and lateral arms, an intake port formed in the vicinity of the front end of the lateral arm, a discharge port provided for one of the horizontal and longitudinal arms, pivotal parts arranged in an area of the apparatus ranging from the intake port to the discharge port, each pivotal part having a ventilating structure to form a ventilating path between the intake port and the discharge port, and a discharge unit arranged in the ventilating path.

DESCRIPTION OF PREFERRED EMBODIMENT

Figure 1:
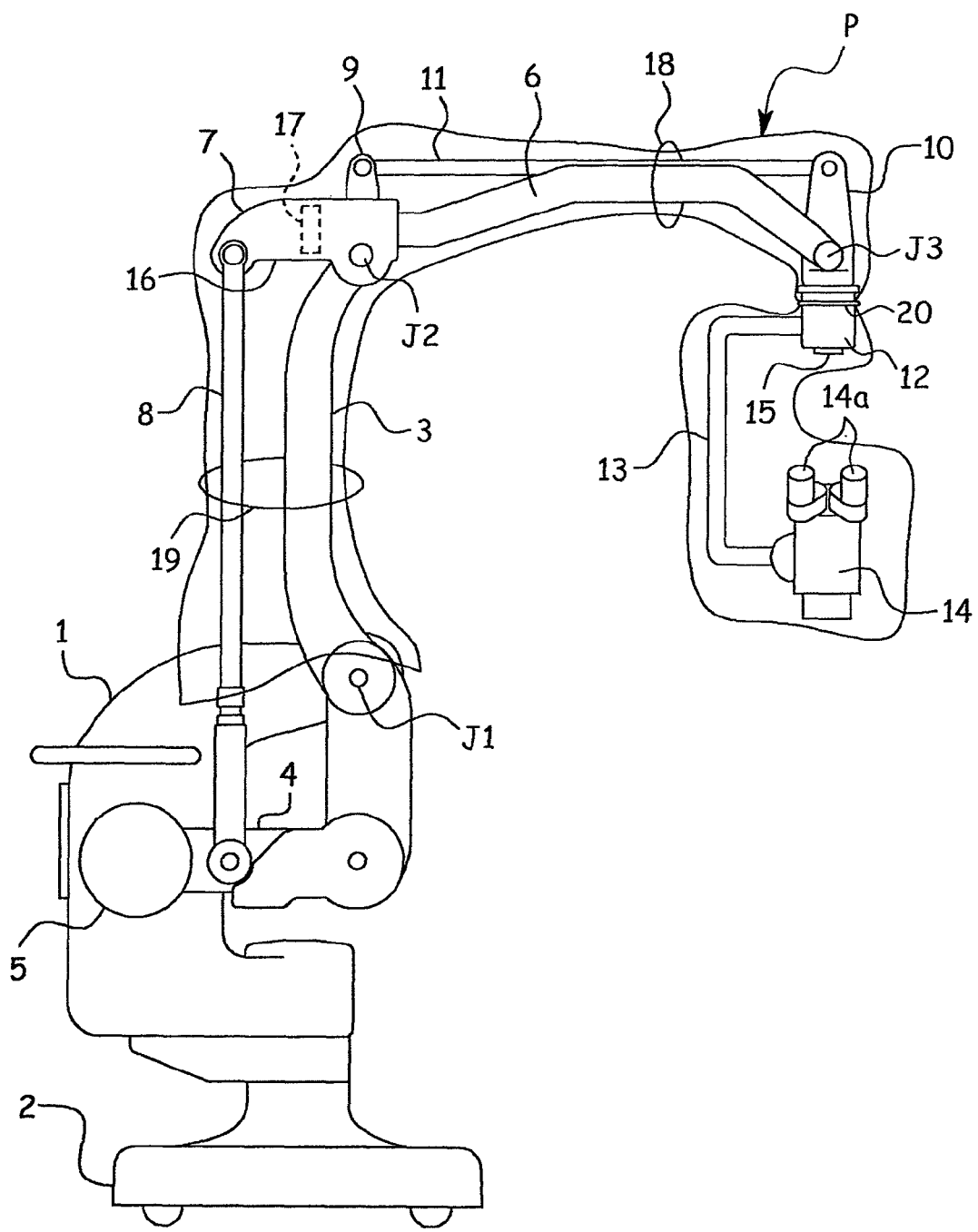
FIG. 1 is a side view illustrating a surgical microscope apparatus according to an embodiment of the present invention.
Figure 2:
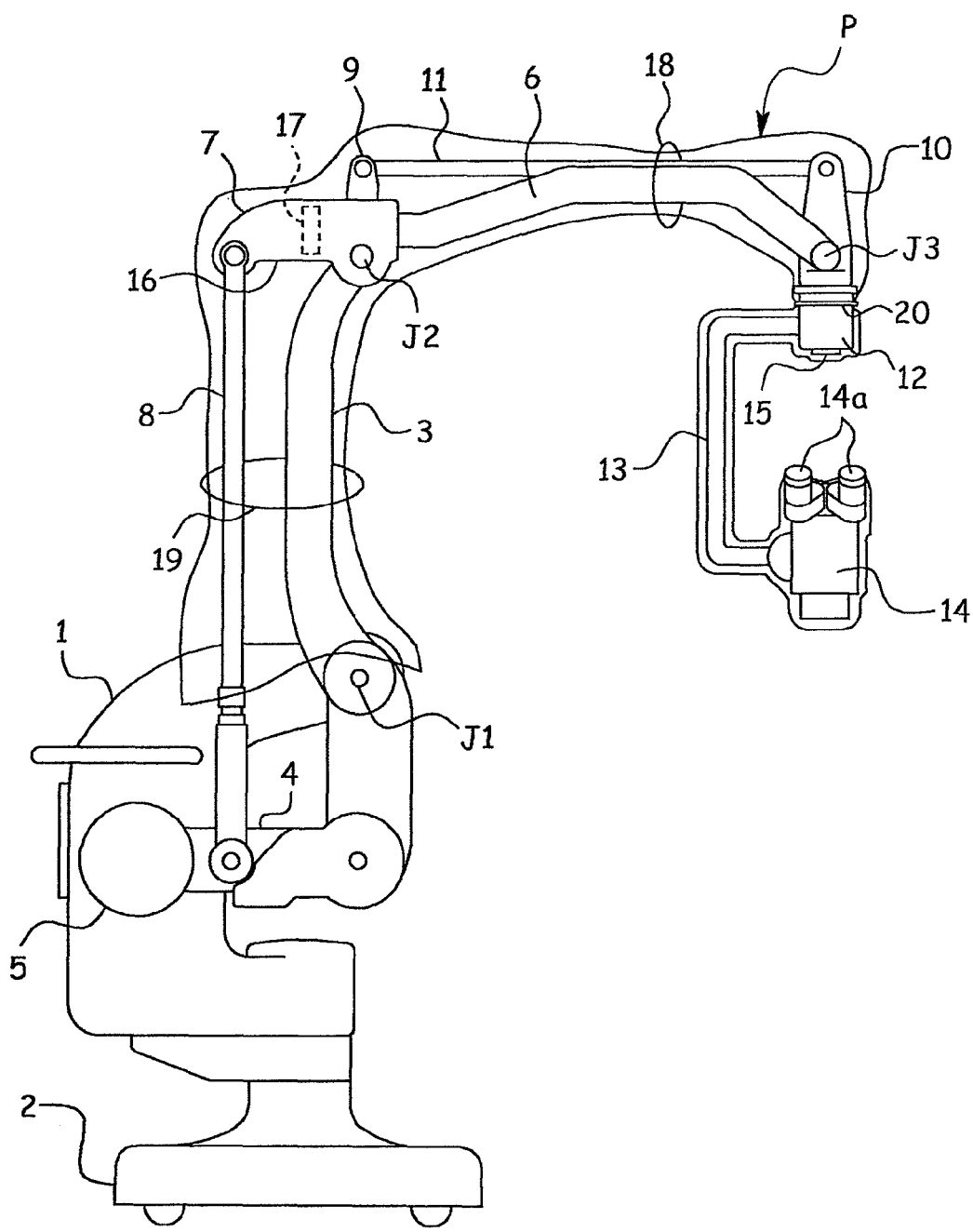
FIG. 2 is a side view corresponding to FIG. 1, illustrating the surgical microscope apparatus with a drape in a drawn state.
Figure 3:
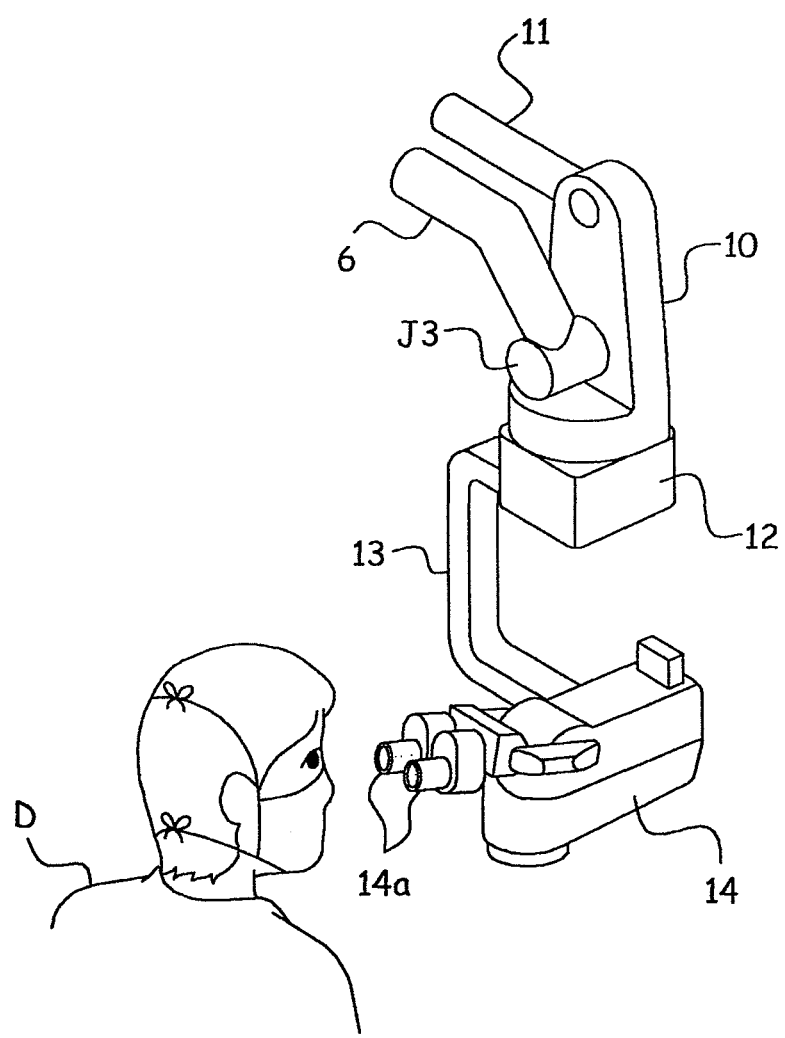
FIG. 3 is aperspectiveview illustrating a surgical microscope of the surgical microscope apparatus and the periphery of the surgical microscope.

A surgical microscope apparatus according to an embodiment of the present invention will be explained with reference to FIGS. 1 to 5.

A stand body 1 of the surgical microscope apparatus is installed on a base 2 that is set on a floor. An upper part of the stand body 1 has a pivotal part J1 that pivotally supports a longitudinal arm (a first arm) 3. The longitudinal arm 3 has a hollow structure and uprightly extends. A lower end of the longitudinal arm 3 is connected to a bar 4, which is connected to a counterweight 5.

An upper end of the longitudinal arm 3 is connected to a lateral arm (a second arm) 6 that has a hollow structure and extends horizontally. The lateral arm 6 has a thick base end 7. The base end 7 has a pivotal part J2 that is connected to the upper end of the longitudinal arm 3. An end of the base end 7 is connected through a longitudinal sub-arm 8 to the bar 4. The longitudinal sub-arm 8 is substantially parallel to the longitudinal arm 3. Four pivotal parts that support the longitudinal arm 3 and longitudinal sub-arm 8 form a parallel linkage.

The base end 7 of the lateral arm 6 has a vertical link 9. With an inner structure (not illustrated) and a lateral sub-arm 11, the vertical link 9 always maintains a vertical (perpendicular) state even if the longitudinal arm 3 or the lateral arm 6 inclines.

The lateral arm 6 is upwardly curved between the base and front ends thereof. The front end of the lateral arm 6 is connected through a pivotal part J3 to a front member 10 that is L-shaped in cross section and has a hollow structure. An upper end of the front member 10 is connected through the lateral sub-arm 11 to an upper end of the vertical link 9. The lateral sub-arm 11 is substantially parallel to the lateral arm 6. The lateral arm 6 and lateral sub-arm 11 are supported with four pivotal parts to form a parallel linkage.

The front member 10 is connected through the lateral sub-arm 11 to the vertical link 9, and therefore, the front member 10 always keeps a vertical position. A lower part of the front member 10 is connected through a pivotal part J4 to a rotary body 12. The rotary body 12 has a box shape and is rotatable around the pivotal part J4. The rotary body 12 is connected to a support arm 13 that supports a surgical microscope 14. With the surgical microscope 14, a surgeon D observes an enlarged image of an objective part of a patient and carries out a surgery.

Figure 4:
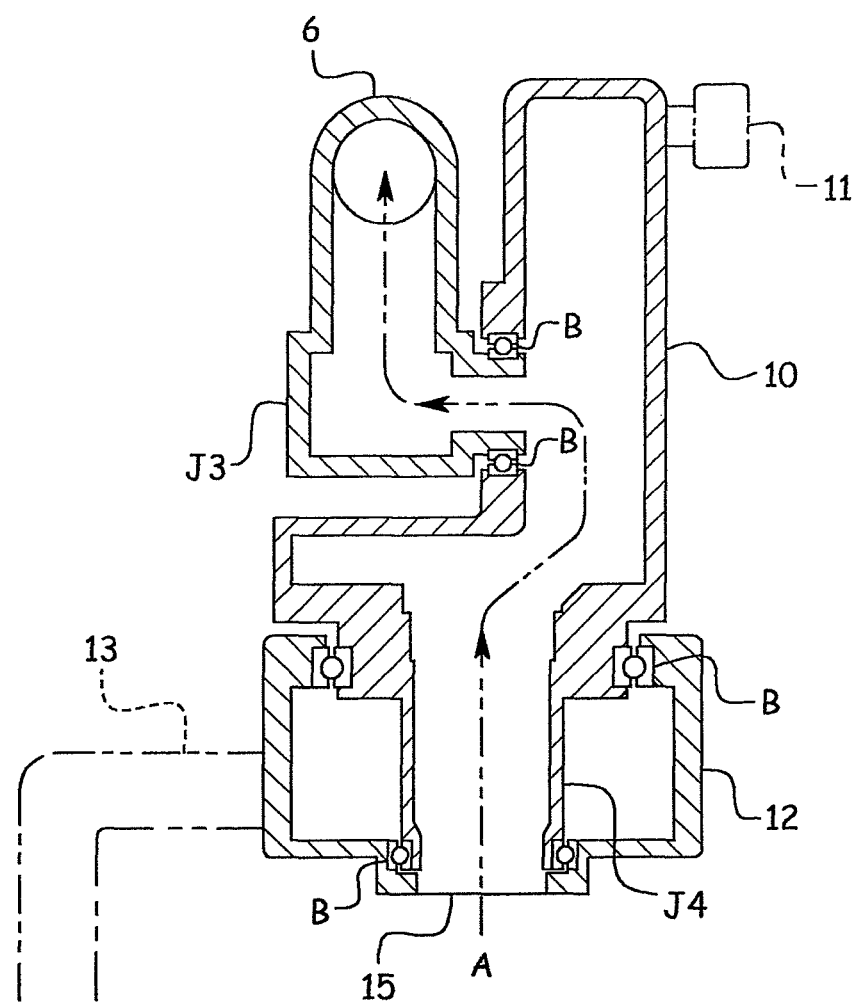
FIG. 4 is a sectional view illustrating a front end area of a lateral arm of the surgical microscope apparatus.

The longitudinal arm 3, lateral arm 6, front member 10, and rotary body 12 each have a hollow structure, to form an inner space of FIG. 4 that is continuous through the pivotal part J3 between the lateral arm 6 and the front member 10 and the pivotal part J4 between the front member 10 and the rotary body 12. This continuous inner space realizes ventilation.

At the pivotal part J3, the lateral arm 6 and front member 10 are connected to each other so that they are rotatable relative to each other through bearings B and communicate with each other.

At the pivotal part J4, the front member 10 and rotary body 12 are connected to each other so that they are rotatable relative to each other through bearings B. A lower end of the rotary body 12 is opened to form an intake port 15. The intake port 15 communicates with an inner space of the front member 10, to form part of a ventilating path A that extends from the intake port 15 to the longitudinal arm 3.

Figure 5:
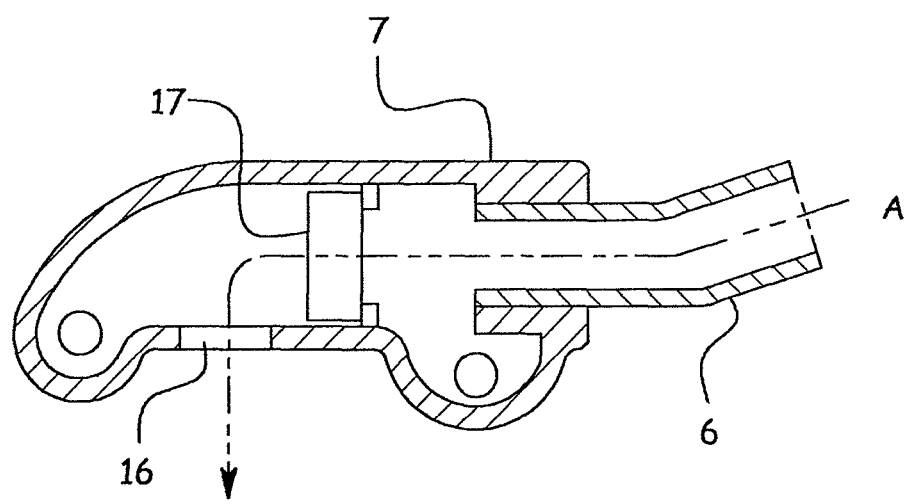
FIG. 5 is a sectional view illustrating a base end area of the lateral arm.

As illustrated in FIG. 5, the base end 7 of the lateral arm 6 includes a discharge port 16 and a discharge fan 17 to serve the discharge unit stipulated in the claims. With this, a closed space (ventilating path A) having two openings (15, 16) is defined through the lateral arm 6 up to the intake port 15. When the discharge fan 17 is driven to discharge air from the inside of the lateral arm 6 to the outside, circumferential air around the rotary body 12 is drawn through the intake port 15, front member 10, and lateral arm 6. The discharge unit generates a pressure gradient to discharge air from the intake port 15 to the discharge port 16 and is arrangeable at any location in the ventilating path A.

Operation of the surgical microscope apparatus covered with a drape P will be explained.

The drape P is put around the surgical microscope 14, lateral arm 6, and longitudinal arm 3. An eyepiece 14a of the surgical microscope 14 is set to protrude out of the drape P. An objective lens of the surgical microscope 14 is provided with a cap (not illustrated).

The drape P distributing around the lateral arm 6 and longitudinal arm 3 is partly fastened with bands 18 and 19 so that the drape P may not sag. The drape P distributing around the rotary body 12 is tightly fastened with a band 20.

In this state, the discharge fan 17 is driven to draw air from around the surgical microscope 14 through the intake port 15 of the rotary body 12. This produces a pressure decrease to firmly attract the drape P only around the surgical microscope 14. Namely, the drape P distributing around the surgical microscope 14 tightly attaches to the surgical microscope 14, to never block the field of vision of the surgeon D. The drape P distributing around the lateral arm 6 and longitudinal arm 3 is not attracted and is only partly bound with the bands 18 and 19. Accordingly, movements of the lateral arm 6 and longitudinal arm 3 are not restricted by the drape P.

The hollow structures of the lateral arm 6 and front member 10 form the continuous inner space that is used as the ventilating path. This eliminates the need of separate suction tubes or the like for drawing air from around the surgical microscope 14.

According to the present embodiment, the rotary body 12 is always maintained at a vertical position, and therefore, the surgical microscope 14 is supported always in a perpendicular state irrespective of movements of the lateral arm 6 and the like. This improves the handling of the surgical microscope 14.

Since the surgical microscope 14 is vertically supported, the motion of the surgical microscope 14 is minimized to rotation around a vertical axis. Accordingly, no problem occurs even when the drape P is tightly attached to the surgical microscope 14.

According to the present embodiment, the discharge unit is arranged in the base end 7 of the lateral arm 6. Instead, the pivotal part J2 between the lateral arm 6 and the longitudinal arm 3 may have a ventilating structure and the discharge unit may be arranged inside the longitudinal arm 3.

According to the present invention, the intake port is formed on the front end side of the lateral arm. By binding a front end part of the lateral arm with a band or the like, the drape put around the surgical microscope apparatus is drawn only around the surgical microscope. Drawing the drape around the surgical microscope clears the visibility of a surgeon who handles the surgical microscope. The drape distributing around the horizontal and longitudinal arms is not drawn, and therefore, the operability of the surgical microscope apparatus is secured. The lateral arm and the like are hollow to form the inner ventilating path, and therefore, there is no need of separately preparing suction tubes or the like for drawing air from the inside of the drape around the surgical microscope.

According to the present invention, the rotary body is kept vertical to secure the vertical state of the surgical microscope even when the lateral arm and the like are widely moved. Due to this, the surgical microscope is easy to handle. Since the surgical microscope is always vertical, the motion of the surgical microscope is minimized to cause no problem when the drape around the surgical microscope is tightly attracted.

This application claims benefit of priority under 35 USC §119 to Japanese Patent Application No. 2012-183003, filed on Aug. 22, 2012, the entire contents of which are incorporated by reference herein. Although the invention has been described above by reference to certain embodiments of the invention, the invention is not limited to the embodiments described above. Modifications and variations of the embodiments described above will occur to those skilled in the art, in light of the teachings. The scope of the invention is defined with reference to the following claims.

What is claimed is:

1. A surgical microscope apparatus having a stand body, a longitudinal arm pivotally supported with the stand body, a lateral arm pivotally supported at a base end thereof by an upper end of the longitudinal arm, a surgical microscope supported at a front end of the lateral arm, and a drape covering a predetermined area of the apparatus ranging from the surgical microscope to the longitudinal arm, comprising:
   a hollow structure provided for each of the longitudinal and lateral arms;
   an intake port formed at the front end of the lateral arm;
   a discharge port provided at one of the lateral and longitudinal arms;
   pivotal parts arranged in an area of the apparatus ranging from the intake port to the discharge port, each pivotal part having a ventilating structure to form a ventilating path between the intake port and the discharge port;
   a discharge unit arranged in the ventilating path; and
   a band tightly sealing the drape around the front end of the lateral arm at the surgical microscope, wherein the drape is tightly held only around the microscope; and
   a front member having a hollow structure, the front member pivotally supported at the front end of the lateral arm; and
   a vertical link connected to the base end of the lateral arm, the front member connected to the vertical link and maintained to be always vertical.

2. The surgical microscope apparatus of claim 1, further comprising:
   a rotary body pivotally supported at a lower end of the front member and rotatable around a vertical axis;
   the intake port formed at a lower part of the rotary body; and
   a pivotal part provided between the front member and the lateral arm and a pivotal part provided between the front member and the rotary body each being configured to pass air along the ventilating path therethrough.

* * * * *

UNITED STATES PATENT AND TRADEMARK OFFICE
CERTIFICATE OF CORRECTION

| | | |
|---|---|---|
| PATENT NO. | : 9,563,045 B2 | Page 1 of 1 |
| APPLICATION NO. | : 13/967588 | |
| DATED | : February 7, 2017 | |
| INVENTOR(S) | : M. Doi et al. | |

It is certified that error appears in the above-identified patent and that said Letters Patent is hereby corrected as shown below:

In the Claims

Column 4, Lines 45, 46 (Claim 1, Lines 17, 18) please change "path; and a" to -- path; a --.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*